United States Patent [19]
Herdle et al.

[11] 4,289,889
[45] Sep. 15, 1981

[54] PREPARATION OF TETRAALKOXYSILANES

[75] Inventors: William B. Herdle, Greenburgh; Bernard Kanner, Nyack, both of N.Y.; Donald L. Bailey, Traverse City, Mich.

[73] Assignee: Union Carbide Corporation, New York, N.Y.

[21] Appl. No.: 163,976

[22] Filed: Jun. 30, 1980

[51] Int. Cl.³ ............................ C07F 7/04; C07F 7/18
[52] U.S. Cl. ............................................................ 556/470
[58] Field of Search .................................................. 556/470

[56] References Cited

U.S. PATENT DOCUMENTS

| | | | |
|---|---|---|---|
| 2,473,260 | 6/1949 | Rochow | 556/470 |
| 2,927,937 | 3/1960 | Gaines | 556/470 |
| 3,072,700 | 1/1963 | de Wit | 556/470 |
| 3,505,379 | 4/1970 | Bonitz | 556/413 |
| 3,557,179 | 1/1971 | Lenz et al. | 556/470 |
| 3,641,077 | 2/1972 | Rochow | 556/470 X |
| 3,709,801 | 1/1973 | Trip | 204/59 |
| 3,775,457 | 11/1973 | Muraoka et al. | 556/470 |
| 3,803,197 | 4/1974 | Anderson et al. | 556/472 X |
| 4,088,669 | 5/1978 | Malek et al. | 556/472 |
| 4,113,761 | 9/1978 | Kreuzburg | 556/470 |

OTHER PUBLICATIONS

Yoorhoeve, "Organohalosilanes: Precursors to Silicones," Elsevier, Amsterdam, p. 129, 1967.

Primary Examiner—Paul F. Shaver
Attorney, Agent, or Firm—Richard J. Gallagher

[57] ABSTRACT

Process for the preparation of tetraalkylorthosilicates which comprises contacting alkanol and dimethylamine with copper-activated silicon, followed by adding alkanol to the resultant silane mixture.

5 Claims, No Drawings

PREPARATION OF TETRAALKOXYSILANES

CROSS-REFERENCE TO RELATED APPLICATION

U.S. patent application Ser. No. 087,797 filed on Oct. 24, 1979, discloses and claims a process for preparing dimethylaminosilanes which comprises reacting dimethylamine with copper-activated silicon particles.

BACKGROUND OF THE INVENTION

1. Field of the Invention

This invention relates to the preparation of tetraalkoxysilanes by the direct reaction of alkanol with silicon.

2. Description of the Prior Art

The most common route of tetraorganooxysilanes is the reaction of silicon tetrahalides with alcohols or their salts. The esters can also be made by transesterification, by reaction of alcohols with $SiO_2$, $SiS_2$, hydridosilanes, or silicon alloys such as $Mg_2Si$ or $Ca_2Si_2$, and by direct reaction of alcohols with silicon.

One such direct reaction involves the formation of alkoxysilanes from alcohols and silicon, ferrosilicon, or iron silicide in the presence of metal alkoxide catalysts. Ethoxysilanes have also been formed by the electrolysis of ethanol with silicon-containing anodes and by the reaction of ethanol with hyperactive silicon formed from calcium silicide and chlorine. Further, silicon can be reacted with alcohols in the presence of copper or copper halides when suspended in liquid such as polycyclic aromatic hydrocarbons or silicone oils. Likewise, copper-catalyzed reactions of silicon with alcohols in the gas phase are known.

U.S. Pat. No. 2,927,937 discloses the use of alkaline catalysts such as ammonia in the direct reaction of ethanol with silicon. U.S. Pat. No. 3,505,379, in column 7, lines 31-36, teaches that tetraethylorthosilicate formation from Si and $C_2H_5OH$ is possible if the reaction be carried out in the presence of basic substances. However this patent teaches, loc cit, that such tetraethylorthsilicate formation should be avoided, presumably because the object of the patented invention is the production of organosilanes. Such prior art generically teaches the equivalence of "alkaline catalyst" and "basic substances" in the reaction in question. Thus, not only does such prior art fail to recognize the importance of employing copper-activated silicon in the reaction, but also it fails to recognize the advantages of utilizing dimethylamine therein.

SUMMARY OF THE INVENTION

It has been found that tetraalkylorthosilicates can be prepared by a process which comprises contacting an alkanol ROH, wherein R is an alkyl group of from one to three carbon atoms, and dimethylamine, wherein the mole ratio of dimethylamine to alkanol is from 0.2:1 to 10:1, with a copper-activated silicon mass, at a temperature in the range of 200° C. through 350° C., to form a silane mixture, and subsequently adding sufficient alkanol ROH to said silane mixture to convert the silanes to tetraalkylorthosilicate. The process shows a high silicon consumption rate which is not accompanied by decling mass activity and decreased fluidization of the reactor.

DESCRIPTION OF THE PREFERRED EMBODIMENTS

The present process for the preparation of tetraalkoxysilanes comprises reacting copper-activated silicon particles with an alkanol selected from the group consisting of methanol, ethanol, propanol, and isopropanol in the presence of dimethylamine.

The silicon particles employed in this invention must be activated with copper for the reaction to be successful. Thus the term, "copper-activated silicon", as employed herein, means any mixture or alloy of copper and silicon that will react with alkanols at elevated temperatures as described herein. In general, two requirements must be fulfilled by a copper-silicon mixture or alloy in order that it be reactive in this invention. The first requirement is that the silicon and copper must be in intimate contact. This may be accomplished, for example, by melting the silicon with the copper, permitting the melt to solidify, and grinding the resulting solid into particles, or alternatively by heating and/or grinding a mixture of silicon and copper particles. It is believed that the copper becomes physically combined with the silicon particles during such treatment such as by diffusion. Another method of preparing a mixture of silicon and copper in suitable intimate contact is to treat silicon particles with copper salts, such as cupric sulfate or cuprous chloride, either by reaction with a solution of the copper salt or by heating. It is believed that copper formed in the resulting reducing process is physically combined with the silicon, such as by deposition or diffusion. Other methods of preparing silicon-copper contact masses, such as those methods conventionally employed for the preparation of silicon-copper mixtures to be reacted with methyl chloride and well-known in the literature for this purpose, may be suitable for this invention. However, such contact masses must satisfy a second requirement beyond the intimate contact of silicon and copper, which is that they must have undergone during or after their preparation a process of activation. Such activation may be conducted by heating an intimate mixture such as those described above under an atmosphere of hydrogen at about 1000° C., or alternatively by treating such a mixture with hydrogen chloride or a compound that releases hydrogen chloride under the activation conditions at a temperature sufficient to permit reaction of the surface of the particles with the hydrogen chloride, e.g. at 300° C. It is believed that this activation step removes oxides from the surface of the silicon-copper particles, and other suitable methods for cleaning the particles and removing surface oxides may be employed for this purpose instead of those just described. For example, conventional methods of activating silicon-copper contact mixtures for reaction with methyl chloride as given e.g. by R. J. H. Voorhoeve, *Organohalosilanes:Precursors to Silicones,* Elsevier Amsterdam, 1967, p. 129, may in some cases be useful for this purpose. Alternatively, the two steps described above may be combined into a single procedure whereby an intimate mixture of copper and silicon is simultaneously formed and activated. This may be accomplished, for example, by treating particles of silicon with solid cuprous chloride in a fluidized bed at about 230°-270° C., in an atmosphere of dimethylamine or of dimethylamine and ethanol.

Moreover, it should be understood that elements other than silicon and copper may be present in the copper-activated silicon, without detracting from the successful practice of our invention. Thus, although hyper-pure silicon may be useful for this invention, provided that it is treated with copper and suitably activated as described herein, commercially available silicon which may typically contain small amounts of other elements such as Al, Bi, Ca, Cr, Cu, Fe, Mn, Ni, Pb, Sn, and Ti, has been commonly employed herein, while mixtures of copper and copper oxides have been used as sources of copper in some preparations. However, the addition of large amounts of certain elements such as Pb is preferably to be avoided because they have an adverse effect on the rate of reaction. Furthermore, additives which have no demonstrable adverse effect on the practice of this invention can be employed, e.g. $ZnCO_3$, which is a well known promoter for the reaction of methyl chloride and silicon, has in some instances been employed during the preparation of the copper-activated silicon.

More specifically, copper-activated silicon particles have been prepared and found useful in this invention in two different ways. One method involved contacting silicon particles and copper in a fluidized bed reactor by fluidizing the silicon particles with hydrogen chloride gas at about 300° C. and adding copper, preferably in the form of a finely divided mixture of copper and copper oxide (about 70–80% copper by weight), commonly known as cement copper, together with a small amount of a promoter such as zinc carbonate, and continuing the process until a vigorous reaction between silicon and hydrogen chloride is established. As a result of said process the copper becomes alloyed to and is widely distributed over the silicon surface. Activation and modification of the reactivity of copper-silicon alloys by hydrogen chloride treatment is well known in the art as seen, e.g. by U.S. Pat. Nos. 2,483,373 and 2,887,501. Alternatively, copper-activated silicon particles employable herein were formed by adding finely divided anhydrous cuprous chloride to the silicon particles as they were fluidized with dimethylamine and ethanol preferably at about 250° C. The reaction of the silicon with ethanol begins almost instantly when the cuprous chloride is added.

The ratio of copper to silicon employed to produce the activated copper-silicon particles employable in this invention is not narrowly critical and the amount of copper need only be that catalytic amount necessary to activate the silicon particles, i.e. render the silicon reactive with dimethylamine and ethanol so as to permit the reaction to proceed at a desirable rate. In general, copper-silicon particles containing between about 0.5 and about 3 percent by weight of copper have been found to provide sufficient activation, although copper-silicon particles containing higher or lower amounts of copper may be employed if desired. Likewise, the particular type of copper compound employed for activation is not critical so long as it is one that will activate the silicon particles. When preforming the copper-activated particles it is preferred to employ a mixture of copper oxides, such as cement copper, while cuprous chloride has been found to be suitable for the in situ method.

During long periods of storage in air or intimate contact with air the copper-activated silicon particles can gradually lose reactivity. This effect is believed to be due to the formation of a surface oxide layer. In addition to air and oxygen, water is also a suspected deactivation agent. Contact of the copper-activated silicon with air or water should therefore preferably be avoided, although storage in air for a few months may be possible without unacceptable loss of activity. However, we have found that reactivity may be restored in copper-activated silicon particles that have lost their activity in this manner. This can be accomplished by subjecting the particles again to one of the activating methods described above, that is, by treating them with hydrogen chloride in a fluidized bed or by adding cuprous chloride or other suitable copper salt to the particles in a bed fluidized with a mixture of dimethylamine and ethanol at ca. 250°–300° C.

The copper-activated particles employable in this invention may be of any particle size commonly employed for solids in conventional gas-solid type reactors. The most preferred particle size in any given reaction will depend upon the type of reactor employed, etc., and the size distribution that will help obtain the optimum results can be easily determined by routine experimentation. For example, in laboratory experiments it was preferred to use the 65 by 150 mesh fraction of said particles because this seemed to produce smoother fluidization in the laboratory reactor, but such size distribution is not necessary for reaction.

The copper-activated silicon particles and gaseous alkanol can be employed in any suitable amounts commensurate with the size of the reactor used and the amount of tetraalkoxysilane product desired. The preferred amounts of reactants will, of course, be those amounts which produce the optimum results, and can be easily determined by routine experimentation. The process of this invention is preferably conducted under autogenous pressure which is generally about 1 atmosphere in a laboratory-scale fluidized-bed reactor; however, subatmospheric or superatmospheric pressures may be employed if desired. The rate of reaction will of course depend upon such factors as the reactants, type of reactor, reaction temperature, etc., employed. Suitable reaction temperatures range from about 200° C. to below the decomposition temperature of the desired product, e.g. 350° C. The preferred reaction temperature range is from 240°–290° C. Since such appears to provide optimum silicon conversion rates in most instances.

The particular type and design of the gas-solid reactor system employed in this invention is not critical and any conventional reactor system, such as a fixed bed reactor, a stirred bed reactor, a fluid bed reactor, or combinations thereof, that is suitable for gas-solid reactions should be applicable for this invention.

In general it is preferred to carry out the process of this invention while the silicon particles are in a state of agitation, such as that caused by a stirred (mechanically agitated) bed reactor or a fluid (gas agitated) bed reactor or a combination of such reactors in which the silicon particles can be agitated by both such methods if desired. More preferably the process of this invention can be carried out in any conventional fluid bed reactor whereby dimethylamine and alkanol gases are fed to the reactor at a rate sufficient to fluidize (suspend and agitate) the bed of silicon particles which are heated in the reactor zone at temperature of about 195° C. to about 400° C., preferably about 240° C. to about 290° C., to thereby produce a gaseous effluent reaction mixture which is then condensed and from which the desired alkoxysilane products can be obtained. Of course, it is understood that the particular operation details of such reactor systems are also conventional and well known in the art and thus need not be fully detailed since such can readily be adapted to and employed in this invention.

For instance, as is common in fluid bed reaction systems the mixture of dimethylamine and alkanol gas in the process of this invention is normally fed to the reactor at a rate at least sufficient to fluidize the bed of silicon particles, but below such a rate that would carry an undesirable amount of unreacted silicon particles beyond the heated reaction zone. The particular flow rate of gas employed for a given process is of course dependent upon such obvious factors as the geometry of the particular apparatus employed, the amount of silicon employed, etc., and may be easily determined and controlled by conventional procedures. If desired, the fluidization of the silicon particles may also be aided by the use of an inert gas such as nitrogen, and the like. However, the use of such an inert gas is not necessary nor generally recommended.

The molar amount of dimethylamine utilized in the initial stage of the process of this invention should be from 0.2 to 10 times the molar amount of alkanol utilized. Preferred dimethylamine:alkanol molar ratios are from 0.8:1 to 5:1. The best results are generally obtained with molar ratios ranging from 1:1 to 3:1.

Addition of dimethylamine to ethanol in the feed actually increases the silicon consumption rate over the rate found with pure alkanol. Even low levels of dimethylamine (i.e. dimethylamine:alkanol ratios below 0.2:1) increase the useful life of the silicon mass. On the other hand, one could theoretically even utilize, in the first state of the present process, dimethylamine alone (i.e. without any alkanol). However, the use of both ethanol and dimethylamine according to the present invention results in a very fast reaction with a longer mass life.

The silane mixture which forms during the initial stage of the present process includes silanes having from one to four alkoxy groups. To the silane mixture is added at least enough alkanol to satisfy all of the silicon valences with alkoxy groups, and generally an excess of alkanol is employed. The addition is normally conducted under ambient conditions, but is can be done at lower or higher temperatures, with the ultimate limits being set by slowness of reaction at the lower temperatures and by decomposition of the desired product at the upper temperatures.

ABBREVIATIONS

In the description which follows, these abbreviations have the meanings indicated:
GLC=Gas Liquid Chromatography
TES=triethoxysilane
TDS=tris(dimethylamino)silane
TEOS=tetraethylorthosilicate
SE-30=a commercial silicone gum
EtOH=ethanol
Me$_2$NH=dimethylamine

Experimental

The following experimental descriptions illustrate the invention. They are not intended to limit the invention in any way. All temperatures are expressed in degrees C. unless otherwise indicated.

Reactor Description and General Procedures

Two reactors were used in this work. Both followed the same basic design for the main reactor tube; however, they differed in size. Feed and product collection components were identical. The reactor tube consisted of a glass tube equipped with the sintered glass frit near the bottom and a sidearm near the top. The tube was wound with two lengths of asbestos-insulated Chromel A wire each having a total resistance of ca. 32 ohms. The first winding covered the entire length of the tube, and was supplied with a constant heating voltage sufficient to keep the upper reactor at 150°–200° C. The second winding covered only the lower third of the reactor, and was supplied with current by a time-proportioning variable temperature controller attached to the reactor thermocouple. Both windings were covered with ca. 1 cm of asbestos paste insulation. An opening was left in the insulation to allow inspection of the bed. The small reactor main tube was 24 mm internal diameter and 62 cm from frit to sidearm. The large reactor tube was 34 mm internal diameter and 64 cm from frit to sidearm. A sidearm (4 mm internal diameter) with a Teflon stopcock (bored to 4 mm opening) was provided in the small reactor 2 cm above the frit for drawing off samples of the mass and for adding solid reactants such as cuprous chloride. The latter procedure was accomplished by placing the finely ground reactant in the sidearm tube and blowing it into the reactor with a stream of dry nitrogen at a pressure higher than that in the bed.

Products were collected by total condensation of effluent with a dry-ice/isopropanol condenser, drawn off through a Teflon valve at appropriate intervals, and concentrated under a flow of nitrogen with the aid of a warm-water bath. The condensate generally contained elutriated fine particles of silicon.

Temperature was monitored with a Type J thermocouple inserted vertically down an axial well in the reactor. The thermocouple was connected both to the temperature controller and to a potentiometric recorder with span calibrated at 30 mv. This arrangement permitted a constant record of temperature vs. time. Temperature was normally recorded with the thermocouple at the bottom of the well, about 5 mm above the frit.

A mercury U-tube manometer connected to the feed stream or to the upper reactor permitted measurement of internal reactor pressure and early detection of plugging gas pathways. Atmospheric pressure was measured with a mercury barometer. Gas flowrates are reported as measured with glass rotameters at ambient temperature and at pressures of 780–810 Torr as measured by this system. The estimated precision of these measurements is ±5%.

Liquid reactants were pumped through Teflon tubing from a nitrogen-purged reservoir to a vaporizer connected just below the inlet frit of the reactor. This consisted of a glass tube ca. 2 cm in diameter packed with 3 mm glass beads and electrically heated to 150°–175° C. The effluent from the vaporizer was mixed with any gaseous coreactant before entering the reactor. Liquid flowrate was monitored with a level gauge attached to the liquid reservoir, and was found to vary considerably with reactor pressure, so that frequent readings were required and the flow values reported are estimated to be accurate to ±10%.

Product Analysis

The crude condensate from each fraction was collected and allowed to stand in a warm water bath under nitrogen. Escaping gases were bubbled through water to trap volatile amines for disposal. GLC analysis was then performed on columns of SE-30, temperature programmed from 50° C. to 75° C. (depending on the instrument used) to 300° C. Using the Hewlett-Packard 5710 gas chromatograph and 8 ft×⅛ inch stainless steel columns packed with 10% SE-30 on Anakrom ABS (90×100 mesh) with 30 cm$^3$/min helium flow, temperature programmed for 75° C. to 300° at 8°/min, the following typical retention times were observed:

| | |
|---|---|
| monomethylamine | 0.58 min |
| dimethylamine | 0.61 min |
| ethanol | 0.96 min |
| bis(dimethylamino)methane | 1.95 min |
| triethoxysilane | 4.10 min |
| tris(dimethylamino)silane | 5.61 min |
| tetraethyl orthosilicate | 6.62 min |

Retention times varied somewhat according to the size of the injection. In ambiguous cases, co-injections of authentic samples were made. TES, TDS, and bis(dimethylamino)methane were isolated from various fractions by preparative gas chromatography and identified by infrared spectroscopy.

EXAMPLE 1

Reaction of Ethanol and Dimethylamine with Silicon

The large reactor was charged with 200 g 65×150 mesh silicon-copper that had been previously etched with HCl but had been stored several months in air. The bed was activated with hydrogen chloride by heating to 320° while fluidizing with nitrogen, then treated with HCl at a flowrate of 4000 cm$^3$/min for 9 min, during which bed temperature rose to 387°. 45.3 g chlorosilanes was collected. The bed was fluidized with nitrogen at 318°14 322° for 0.7 hr, then purged with nitrogen at a reduced flowrate overnight. The mass was then fluidized again with nitrogen and heated to 257°. Reactants were then fed at the Feed Rates described in Table 1. Fractions were collected as shown in Table 1 and concentrated at room temperature to remove excess Me$_2$NH. Temperatures varied widely during collection of C and subsequent fractions. Because of exothermicity the reaction sustained the reactor temperature without external heating, bypassing the automatic temperature controller. The mass began to appear reddish during collection of C. Raising the thermocouple from the bottom of the bed approximately 8 cm caused a drop of ca.10° C. in the temperature reading. Raising the thermocouple 15 cm caused 50° drop during D. The observation indicated that a highly exothermic reaction was taking place in the first few cm of gas-solid contact. A superficial linear gas flowrate of approximately 13 cm/sec was calculated during D, assuming an empty reactor. Thus a substantial fraction of the reaction heat must have been liberated with 0.1 sec after gas and solid met. After the ethanol feed was stopped at the end of G, the flowrate of nitrogen needed to circulate the bed particles was considerably greater than that needed before A, despite the reduced bed volume. When the mass was emptied from the reactor, it was somewhat sticky, and a considerable part of it adhered to the reactor walls. 34.7 g of Si(Cu) was recovered, excluding that portion adhering to the reactor (estimated at less than 10g). Calculation based on isolated products predicted that 53.7 g should have been recovered. Thus approximately 90% of the silicon consumed and elutriated was accounted for. The error was ascribed mainly to the crude analysis procedure (no internal standard measurements were made) and to calculation approximations, but the possible existence of unisolated volatile products cannot be excluded. The small amount of product isolated in H was assumed to have been washed from the condenser, not formed from alkanol, in view of its heavies-rich composition and the presence of the ethanol that must in any case have derived from hold-up. Examination of the product analyses showed that when excess ethanol was present only relatively few products were found, probably because of complete substitution of Si-OEt for Si-H and SiNMe$_2$. The evolution of water-insoluble gas from the condensate suggested that at least some of this substitution took place in the liquid phase.

TABLE 1

Reaction of Ethanol and Dimethylamine with Silicon

A. Reaction Parameters

| Fraction | Duration (hr) | Temp. (°C.) | Feed Rates [a] EtOH | Feed Rates [a] Me$_2$NH | Feed Rates [a] N$_2$ | Mole Rate EtOH/Me$_2$NH | Crude Liquid Condensate (g) |
|---|---|---|---|---|---|---|---|
| A | 0.49 | 249–253 | 0 | 3530 | 370 | 0 | 0 |
| B | 0.83 | 249–253 | 0 | 3530 | 370 | 0 | 41.1 |
| C [b] | 0.86 | 260–283 | 2440 | 3530 | 390 | 0.69 | 261.8 |
| D | 0.98 | 267–289 | 2560 | 3530 | 350 | 0.73 | 248.2 |
| E | 0.87 | 256–288 | 2540 | 3530 | 310 | 0.72 | 216.4 |
| F | 0.99 | 241–260 | 2550 | 3530 | 310 | 0.72 | 255.0 |
| G | 0.79 | 220–259 | 2550 | 3530 | 310 | 0.72 | 238.3 |
| H [c] | 0.4 | 245–250 | 0 | 7270 | 350 | 0 | 0.9 |

Notes:
[a] cm$^3$/min at 250° C./788 Torr, calculated from room temperature data using ideal gas law.
[b] Condensate was discarded for 0.12 hr prior to C while ethanol flow stabilized.
[c] The bed was fluidized with nitrogen for 0.2 hr prior to H.

B. Product Analysis

| Fraction | EtOH | TDS | TES | TEOS | monosilanes [e] | heavies [f] | Mean Si Consumption Rate (% per hr) |
|---|---|---|---|---|---|---|---|
| B | 0 | 74.7 | 0 | 0 | 5.1 | 2.2 | 3.5 |
| C | 0 | 12.8 | 32.4 | 0.3 | 27.9 | 0.6 | 22.7 |
| D | 0 | 2.4 | 27.9 | 25.4 | 28.5 | 2.4 | 23.2 |
| E | 0 | 3.1 | 26.6 | 46.0 | 14.3 | 1.7 | 31.6 |
| F | 9.1 | 0 | 0 | 57.9 | 0.5 | 1.6 | 26.8 |
| G | 18.6 | 0 | 0 | 30.2 | 0.6 | 1.7 | 21.0 |

TABLE 1-continued

Reaction of Ethanol and Dimethylamine with Silicon

| H | 17.1 | 0 | 0 | 42.8 | 10.3 | 25.2 | 0.2 |

Notes:
[d] Percent of total GLC peak area. Residual area is Me$_2$NH and unidentified peaks of retention times less than 2 min.
[e] Unidentified peaks of retention times 2–7.0 min (TEOS = 5.5 min).
[f] Peaks of retention times greater than 7.0 min.

EXAMPLE 2

Reaction of Ethanol and Dimethylamine with Silicon at Various Mole Ratios

The large reactor was charged with 200 g 65×150 mesh silicon-copper (0.9% Cu) that had been previously etched with HCl but had been stored several months in air. This was activated by heating the bed to 323° with nitrogen fluidization and treating with anhydrous HCl at 4000 cm$^3$/min for 0.18 hr, during which bed temperatures rose to 380° and 63.2 g chlorosilanes was collected. The bed was then purged with nitrogen, fluidizing at 250° for 1.1 hr.

The mass was kept at room temperature overnight under a flow of nitrogen, then heated to 259° with nitrogen fluidization. Dimethylamine and ethanol were introduced and fractions were collected as shown in Table 2. Each fraction was concentrated at room temperature under nitrogen to remove excess dimethylamine. During the course of the reaction the temperature, the aerosol density below the condenser, and the evolution rate of water-insoluble gas varied greatly, but the overall trend was downward in each case. A gradual decrease in aerosol density was noted during the fraction D, accompanied by a distinct downward trend in bed temperature, so that the automatic temperature controller began to supply heat midway through the fraction. When the dimethylamine flowrate was increased at the start of E, a 6° temperature rise was seen, and a corresponding equal drop took place when the flowrate was cut back again at the start of F. Corresponding qualitative change in aersol density and rate of gas evolution from the trap were noted: both increased at the start of E and decreased at the start of F. The temperature rose somewhat around the midpoint of F, then fell again. Similar increases in temperature, aerosol density, and gas evolution rate were noted when the dimethylamine feed rate was raised in fraction H, and aerosol density decreased again as soon as the flowrate was decreased in I. Temperature and gas evolution rate fell more slowly. Particle circulation became less vigorous as the reaction progressed until after fraction J a nitrogen flow of ca. 4000 cm$^3$/min at 25° C. (double that needed for good mass circulation before the reaction) was insufficient to agitate all the particles. During J, ethanol feed rate was increased 17%, over its value in I, then lowered again. Dimethylamine feed rate was also raised substantially and lowered. None of these changes caused any appreciable temperature perturbation, the aerosol density remained fairly low, and the hydrogen evolution rate remained at low levels. It was concluded that the mass was irresversibly losing its activity, and the experiment was stopped. When the mass was recovered from the reactor, 67.0 g. was readily poured out (including several "clinkers" of agglomerated particles, roughly 5 mm in diameter), but an additional 59.8 g coated the reactor walls in a hard layer up to 6 mm thick and was removed only after soaking in aqueous potassium hydroxide. GLC analysis showed excess ethanol in all fractions after C, and nearly all of the product was TEOS and "heavies" assumed to be perethoxyoligosiloxanes. Internal standard injections showed weight and area percents to be nearly equal for three fractions; therefore, area percents were used, after application of a correction factor, in the calculations. On the basis of isolated products, 134.6 g was calculated as the amount of silicon remaining in the reactor vs. 126.8 g actually recovered. Thus 89.3% of the consumed mass was accounted for.

Distillation of the product of fraction D (134.7 g, 42.7% TEOS by GLC (corrected) gave 51.5 g forerun (88% ethanol and 12% dimethylamine by GLC), 53.7 g TEOS (99.9%, bp 166°-7° C.), and 20.1 g pot residue (29% TEOS with the remainder "heavies" assumed to be oligosiloxanes). Recovered TEOS represented 40% by weight of the original product weight, with another 4% left in the pot, in good treatment with the composition estimated by GLC. Thus little disproportionation probably occurred during distillation.

TABLE 2

Variation of Feed Ratios

A. Reaction Conditions

| Fraction | Temp. (°C.) | Duration hr | Flowrates [a] Me$_2$NH | EtOH [b] | N$_2$ | Mole Ratio EtOH/Me$_2$NH |
|---|---|---|---|---|---|---|
| A | 250–254 | 0.83 | 3510 | 0 | 579 | — |
| B | 252–258 | 1.06 | 3510 | 0 | 579 | — |
| C [c] | 258–270 | 0.19 | 828 | 4520 | 544 | 5.4 |
| D | 255–270 | 0.39 | 828 | 4790 | 825 | 5.6 |
| E | 253–260 | 0.33 | 3510 | 4790 | 263 | 1.3 |
| F | 250–266 | 0.90 | 1400 | 4830 | 0 | 3.3 |
| G [d] | 245–261 | 0.45 | 1400 | 4800 [d] | 0 | 3.3 [d] |
| H | 245–260 | 0.41 | 3510 | 4510 | 0 | 1.2 |
| I | 250–262 | 0.93 | 1400 | 4570 | 527 | 3.1 |
| J [e] | 243–249 | 1.07 | 2060 [e] | 5050 [e] | 421 [e] | 2.3 [e] |

Notes:
[a] cm$^3$/min at 250° C./794 Torr, calculated using ideal gas law from volumes measured at 25° C.
[b] calculated using Van der Waals' equation of state (CRC Handbook: a = 12.02, b = 0.08407).
[c] Condensate was discarded during 0.08 hr prior to C while ethanol flow was established.
[d] Ethanol flow stopped briefly during G.
[e] Flowrates were varied during J. Time - averaged values are reported.

B. Product Analysis

TABLE 2-continued

Variation of Feed Ratios

| Fraction | Product Analysis [f] | | | | | Mean Si Consumption Rate (%/hr) |
|---|---|---|---|---|---|---|
| | EtOH | TDS | TEOS | monomer [g] | heavies [h] | |
| A | — | — | — | — | — | 0 |
| B | — | 74.8 | — | 4.2 | 5.5 | 3.8 |
| C | 21.3 | 0 | 55.3 | 1.5 | 12.3 | 17.2 |
| D | 38.6 | 0 | 41.7 | 1.2 | 7.8 | 13.9 |
| E | 39.6 | 0 | 8.3 | 1.5 | 4.3 | 5.3 |
| F | 49.5 | 0 | 10.7 | 1.5 | 5.4 | 5.5 |
| G | 50.8 | 0 | 8.1 | 1.1 | 4.6 | 3.6 |
| H | 41.9 | 0 | 12.1 | 0.3 | 3.0 | 6.8 |
| I | 49.2 | 0 | 7.7 | 1.0 | 4.0 | 4.3 |
| J | 55.0 | 0 | 2.0 | 0.5 | 1.2 | 1.5 |

Notes:
[f] GLC area percents. Residue is mainly dimethylamine.
[g] Other peaks of retention time below 10 min (TEOS = 5.8 min).
[h] Peaks of retention time above 10 min.

On the basis of this experiment the following conclusions were reached. At higher ethanol: dimethylamine ratios (in the range of 3–5) the mass degrades more quickly than at the previously-used ratios near unity. In view of the extensive caking and agglomeration of the residual mass recovered from the reactor, reversible by soaking in aqueous potassium hydroxide, it appears that "heavies" accumulated in the bed, restricting mass circulation and gas flow. This alone could account for much of the decrease in mass performance, but destruction or blockage of active sites may also be implicated. The reaction appears to be faster when more dimethylamine is present in the feed. All four reaction rate monitors (temperature, gas evolution, aerosol, and isolated products) indicated increased rates when the ethanol: dimethylamine ratio was decreased from 3–4 to 1.2–1.3. This implies that the presence of dimethylamine actually enhances the rate at which ethanol reacts with silicon-copper.

EXAMPLE 3

Requirement that a Catalyst be Present for the Ethanol/Dimethylamine/Silicon Reaction The small reactor was charged with 102.4 g commercial metallurgical grade silicon, 65×150 mesh. This bed was fluidized with nitrogen and heated to 320°, then fluidized with anhydrous hydrogen chloride at 319°–333° for 17 min, collecting 14.4 g chlorosilanes. The bed was purged with nitrogen for 1.5 hr, then cooled to room temperature and held under a positive nitrogen pressure overnight.

In the morning, the bed was heated to 258° while fluidizing with nitrogen. Dimethylamine was substituted for nitrogen at 1300 cm$^3$/min (298° K., 781 Torr) and fractions were collected as shown in Table 3. The bed showed no reactivity toward dimethylamine alone or toward a mixture of dimethylamine and ethanol until after copper was added during fraction F. This addition was accomplished by blowing into the reactor with a nitrogen stream through a port just above the bottom of the bed a mixture of 150 mesh HCl-activated copper-treated silicon of the kind used in Example 1 (0.84 g) and finely ground cuprous chloride (1.27 g), so that the total copper introduced was 0.86 g. A gradual temperature rise and formation of silicon-containing products began at once. After condensation of the products and concentration at room temperature to remove excess dimethylamine, gas chromatographic analysis of fraction F-J showed up to 47 separate peaks. For purposes of analysis, these were grouped into three categories: low-boiling materials containing no silicon, monomeric silanes, and "heavies", according to whether their retention times on the SE-30 column were less than or greater than that of tetrakis (dimethylamino)silane. In fractions F and G, excess ethanol was present, so that essentially all monosilanes were present as TEOS. In fractions H–J, no free ethanol was present in the condensed concentrated products, and triethoxysilane was the main constituent, contributing 30–42% of total gc peak area.

This example demonstrates the requirement that a catalyst such as copper be present to obtain reaction between silicon and mixtures of alkanol and dimethylamine in the fluidized bed at ca. 250° C.

TABLE 3

CuCl Addition to Initiate Reaction

| Fraction | Temp. (°C.) | Duration (hr) | Flowrates [a] | | Crude Condensate (g) | Analysis [b] Monomeric Silanes | heavies [c] | Si consumed (%/hr) |
|---|---|---|---|---|---|---|---|---|
| | | | EtOH | Me$_2$NH | | | | |
| A | 253–255 | .92 | 0 | 55 | 0 | — | — | 0 |
| B | 253–254 | .86 | 0 | 55 | 0 | — | — | 0 |
| C | 252–254 | .58 | 14 [d] | 65 | 47.5 | — | — | 0 |
| D | 252–253 | .69 | 14 | 65 | 88.5 | — | — | 0 |
| E | 250–252 | .66 | 23 | 65 | 123.8 | — | — | 0 |
| F [e] | 248–256 | .52 | 14 | 65 | 58.1 | 12.98 | 1.14 | 2.7 [f] |
| G | 254–257 | .83 | 14 | 65 | 61.6 | 62.33 | 2.48 | 6.9 |
| H | 256–260 | .67 | 14 | 65 | 60.5 | 63.59 | 3.15 | 11.3 |
| I [g] | 254–260 [g] | .61 | 14/0 [g] | 65 | 41.5 | 82.46 | 2.59 | 12.2 |

TABLE 3-continued

| | | | | | Crude | Analysis [b] | | |
|---|---|---|---|---|---|---|---|---|
| | Temp. | Duration | Flowrates [a] | | Condensate | Monomeric | | Si consumed |
| Fraction | (°C.) | (hr) | EtOH | Me₂NH | (g) | Silanes | heavies [c] | (%/hr) |
| J | 254–256 | .24 | 0 | 65 | 0.1 | 79.66 | 18.49 | 0.05 |

[a] mmol/min
[b] gas chromatographic area percents
[c] peaks eluting after Si(NMe₂)₄ on an SE-30 column
[d] EtOH flow was begun 0.06 hr into the fraction, and rose to this value
[e] 1.27 CuCl and 0.84g SiCu were blown into the bed by a nitrogen stream 0.10 hr into fraction F.
[f] assumes all products were formed after CuCl introduction
[g] EtOH flow was stopped 0.45 hr into fraction I. Bed temperature fell from 259–260° to 254–256° at that time.

EXAMPLE 4

Effect of Water and Air on the Reaction of Ethanol and Dimethylamine with Silicon The small reactor was charged with 100.79 g 65×150 mesh silicon-copper (0.9% Cu) that had been previously HCl-etched but stored in air. The bed was heated to 320° and fluidized with anhydrous HCl at a flowrate of 2000 cm³/min for 12.6 min during which bed temperature rose to 345° then fell slowly to 330° and 35.9 g chlorosilanes was collected. The bed was then fluidized with nitrogen at 315° for 0.8 hr and at 250° for 2.3 hr. Dimethylamine was introduced, followed by ethanol. Fractions were collected as shown in Table 4. Injections of water (total of 150 μl) during fraction C did not adversely affect reaction rate. No decrease in reactor temperature was noted, and the silicon consumption rate calculated from the product distribution was greater than for any other fraction. Injection of air (50 cm³) in fraction E did decrease reaction rate, as reflected in the calculated silicon consumption rate as well as in a bed temperature decrease. This loss of activity seems to have been reversed with time, but the rate never recovered to the levels of B and C. During fraction D, when the ethanol feed was turned off, the bed retained its activity toward dimethylamine. Some ethoxy-substituted products were apparently washed from the reactor or the condenser during the fraction, but the overall resemblance of the product analysis to that of A rather than B or C clearly indicates that dimethylamine had reacted directly.

TABLE 4

Effect of Water and Air

A. Reaction Parameters

| Fraction | Duration (hr) | Temp. (°C.) | Feed Rated [a] | | | Mole Ratio |
|---|---|---|---|---|---|---|
| | | | Me₂NH | EtOH | N₂ | EtOH/Me₂NH |
| A [b] | 1.06 | 251–153 | 2290 | 0 | 400 | 0 |
| B [c] | 0.59 | 251–259 | 2290 | 820 | 400 | 0.36 |
| C [d] | 0.76 | 255–259 | 2290 | 770 | 400 | 0.34 |
| D | 0.64 | 253–254 | 2290 | 0 | 400 | 0 |
| E [e] | 0.54 | 255–258 | 2290 | 790 | 400 | 0.35 |
| F | 0.30 | 253–258 | 2290 | 790 | 400 | 0.34 |

Notes:
[a] cm³/min at 250° C./796 Torr, calculated from room temperature data using ideal gas law.
[b] A slight exotherm associated with the onset of reaction occurred after 0.45 hr.
[c] Ethanol flow was started 0.3 hr after start of fraction.
[d] 50 μl water was injected at 0.03 hr and 100μl water at 0.79 hr into the fraction. Ethanol was turned off 0.72 hr into the fraction, and temperature fell to 253–245°.
[e] 50 ml air was injected 0.41 hr after start of fraction. Temperature fell to 248° at once, but recovered to 253–256° within 2 min.

B. Product Analysis

| Fraction | GLC Analysis [f] | | | | | Mean Si Consumption Rate (% per hr) |
|---|---|---|---|---|---|---|
| | ETOH | TDS | TEOS | monomer [g] | heavies [h] | |
| A | 0 | 75.1 | 0 | 5.3 | 1.3 | 4.3 |
| B | 0 | 27.3 | 0.2 | 55.3 | 0.9 | 20.9 |
| C | 0 | 20.3 | 1.1 | 59.0 | 3.3 | 21.8 |
| D | 0 | 73.8 | 0.3 | 8.1 | 1.8 | 10.4 |
| E | 0 | 9.2 | 23.2 | 37.0 | 5.8 | 15.3 |
| F | 0 | 0.5 | 30.3 | 34.1 | 5.9 | 17.6 |

Notes:
[f] Percent of total GLC peak area. Residue is dimethylamine and unidentified peaks of retention times less than 2 min.
[g] Unidentified peaks of retention times 2.0–7.5 min (TEOS = 6.7 min).
[h] Peaks of retention times greater than 7.5 min.

EXAMPLE 5

Reaction of Ethanol with Silicon-Copper in the Absence of Dimethylamine

The small reactor was charged with 108.42 g 65×150 mesh silicon-copper (0.9% Cu) that had been activated with hydrogen chloride but had subsequently stood several months in air so that reactivation seemed advisable. Therefore the bed was heated to 315° C. while fluidizing with nitrogen, and anhydrous hydrogen chloride was administered, replacing nitrogen, at a flowrate of 2200 cm³/min. During the following 8.6 min, bed temperature ranged from 315°–348° and 27.9 g chlorosilanes was collected at the dry ice condenser. The hydrogen chloride flow was then disconnected, and the bed was purged with nitrogen at 250°–315° for 5 hr, then overnight at room temperature.

In the morning, the bed was again fluidized with nitrogen and heated to 260°. Ethanol was fed to the bed through a vaporizer maintained at 150°, and fractions were collected as detailed in Table 5. In addition to ethanol, a cofeed of nitrogen was required to maintain circulation of the particles in the bed. This became increasingly difficult as the reaction progressed. By the end of the first hour of ethanol feed, it was impossible to circulate the particles at bed bottom with the nitrogen flow. When the mass was examined at the end of the reaction period, it was spongy and sticky. A total of 83.4 g of the mass was recovered, but a further quantity (estimated at 1 g) stuck to the walls of the reactor. Thus, less than 19.2 g of the original silicon-copper charged (19% of the bed remaining after HCl etching) was consumed by ethanol in the 4.1 hr of reaction. Analysis of the fraction weights and compositions yielded the mean reaction rates given for each fraction in the last column of Table 5. The initial rate of 12.4% /hr silicon consumption in fraction A deteriorated rapidly with time. Some recovery occurred in fraction E when the ethanol feed rate was increased, increasing slightly the vigor of particle circulation in the bed and the concentration of ethanol in the feed gas, but the rate again declined thereafter despite further increases in the ethanol feed rate. Fresh copper catalyst, added just before the start of fraction I, again permitted a temporary resurgence of the reaction rate, though not to its original value. Reaction rate continued to decline thereafter.

This example demonstrates the difficulties encountered in the gas-solid reaction of ethanol with silicon-copper in a fluidized bed, especially declining mass activity and the stickiness of the mass that coats reactor walls and hinders fluidization. The example also provides silicon consumption rates for the ethanol-silicon-copper reaction that may be compared with those obtained in the presence of amine according to our invention, as illustrated by the other examples.

A. Reaction of Ethanol and Monomethylamine with Silicon

The small reactor was charged with 100.35 g silicon-copper (0.9% Cu) that had been HCl-etched but stored in air. The bed was activated with anhydrous hydrogen chloride after heating to 320° while fluidizing with nitrogen. HCl was administered at 2000 cm$^3$/min for 12 min, during which bed temperature rose to 339° and 33.8 g chlorosilanes was collected. After 2.6 hr of fluidization with nitrogen, dimethylamine was introduced, followed by ethanol and monomethylamine, as shown in Table 6. At the end of the experiment, the reactor contained 50.8 g Si(Cu). Calculations based on the isolated products and estimates of elutriated fines predicted 52.5 g, so that 96% of the mass consumed after HCl activation was accounted for. A total of 25.0 g Si(Cu) (28% of the activated bed) was consumed after HCl activation, and 5.0 g (6% of the activated bed) was elutriated. The mass showed activity toward dimethylamine in fraction B, but this activity was lost in fraction I. The mass also declined in its activity toward ethanol-dimethylamine, beginning when monomethylamine was first introduced in E. However, this decline did not appear to be serious until after dimethylamine flow was discontinued in G. Simultaneously, fluidization difficulties were encountered at the bottom of the bed. The constantly changing character of the mass makes precise evaluation difficult, but comparison with similar experiments in the same reactor suggests that the mass-life prolongation effect of dimethylamine on the ethanol reaction is exhibited to a lesser degree or not all by monomethylamine. However, monomethylamine does not instantly poison the ethanol reaction as it does the dimethylamine-silicon reaction.

By preparative gas chromatography, a sample of a peak appearing at the retention time of 1.9 min. was isolated from the products of fraction I and identified by infrared spectroscopy as bis(dimethylamine)methane. It accounted for 16.7% of the total peak area of the fraction, and was also found in fraction H, accounting for 0.4% of total peak area. This material is a product of dimethylamine cracking.

B. Reaction of Diethylamine/Ethanol with Silicon-Copper

The small reactor was charged with 130 g silicon-copper (0.9% Cu). This bed was fluidized with nitrogen

TABLE 5

Reaction of Ethanol without added amine

| Fraction | Duration (hr) | EtOH flow (g/min) | N$_2$ flow (cm$^3$/min) | Temp. (°C.) | Crude condensate (g) | GLC analysis [a] | | | | Mean Si consumption rate (%/hr) |
|---|---|---|---|---|---|---|---|---|---|---|
| | | | | | | EtOH | SiH(OEt)$_3$ | TEOS | heavies [b] | |
| A | 0.27 | 0-3.3 | 0-600 | 275-290 | 38.76 | 27.64 | 11.45 | 21.86 | 7.07 | 12.4 |
| B | 0.18 | 3.6 | 600 | 250-280 | 37.36 | 68.93 | 0.40 | 24.40 | 4.01 | 8.4 |
| C | 0.22 | 3.6 | 600 | 258-262 | 40.84 | 85.44 | 0.01 | 11.80 | 1.58 | 3.5 |
| D | 0.33 | 3.8 | 600 | 255-263 | 63.64 | 90.41 | 0.01 | 7.18 | 0.75 | 2.2 |
| E | 0.23 | 4.2 | 600 | 257-261 | 59.70 | 87.75 | 0 | 10.09 | 0.87 | 4.1 |
| F | 0.38 | 4.7 | 600 | 251-255 | 104.00 | 91.97 | 0 | 5.57 | 0.47 | 2.4 |
| G | 0.27 | 4.7 | 600 | 250-254 | 73.22 | 95.51 | 0 | 2.71 | 0.21 | 1.2 |
| H [c] | 0.28 | 4.7 | 600 | 249-253 | 77.87 | 96.66 | 0.04 | 1.78 | 0.15 | 0.8 |
| I | 0.22 | 4.7 | 600 | 250-266 | 51.40 | 80.34 | 4.38 | 6.21 | 5.63 | 6.3 |
| J | 0.33 | 4.7 | 600 | 254-258 | 84.21 | 89.71 | 0.14 | 4.43 | 2.04 | 2.6 |
| K | 0.33 | 4.7 | 600 | 253-257 | 83.10 | 93.71 | 0.52 | 4.25 | 0.82 | 2.2 |
| L | 0.68 | 4.8 | 600 | 252-254 | 187.93 | 95.68 | 0.56 | 2.74 | 0.49 | 1.7 |
| M | 0.38 | 4.8 | 600 | 248-254 | 113.11 | 97.02 | 0.33 | 1.73 | 0.40 | 1.1 |

[a] gas chromatographic area %
[b] total peaks eluting after TEOS
[c] 0.72g CuCl was blown into the bed 0.02 hr before the end of fraction H.

EXAMPLE 6

Effect of Bases other than Dimethylamine

This example illustrates the effect of various bases other than dimethylamine on the alkanol-silicon/copper reaction.

and heated to 310°, then treated with anhydrous hydrogen chloride, replacing nitrogen at 2200 cm³/min. Bed temperature rose rapidly to 324°-328° and 40.3 g chlorosilanes was collected during the next 0.24 hr. The bed was purged with nitrogen for 1.3 hr at ca 310°, then overnight at a reduced flowrate at room temperature.

In the morning, the bed was fluidized with nitrogen and reheated to 252°. Dimethylamine was introduced at 1370 cm³/min (room temperature flowrate). During the next 3.79 hr at 249°-252° products were collected that after concentration to reduce their dimethylamine content were analyzed and found to contain 12.1 g silicon as aminosilanes.

The dimethylamine feed was replaced with a 1:1 (v:v) mixture of diethylamine (dried by distillation from calcium hydride) and ethanol (200 proof) at an overall feed rate of 2.9 cm³/min with a 100 cm³/min cofeed of dry nitrogen to maintain fluidization of the bed. After an adjustment period of 0.3 hr during which the bed temperature varied within the range 244°-259° C. during flow adjustments, bed temperature stabilized at 251°-256° C. The ethanol/diethylamine cofeed was continued for a total of 1.4 hr with bed temperature remaining in that range. The products isolated during that time resembled those of the reaction of silicon with ethanol alone. TEOS was the major product (initially accounting for 71% of the GLC peak area excluding reactants) but diminished in intensity with time. Calculations based on isolated products showed a maximum silicon consumption rate of 2.8%/hr during the ethanol/diethylamine cofeed, steadily dropping to ca 0.6%/hr at the end of the experiment.

This example shows that diethylamine is ineffective in enhancing rates of silicon consumption and in prolonging bed life when added to the ethanol feed in the reaction of ethanol with silicon at ca 250° C. in a fluidized bed.

C. Effect of Ammonia on the Ethanol-Silicon/Copper Reaction

The small reactor was charged with 100.2 g HCl-activated silicon-copper that had been stored in air. The bed was heated with nitrogen fluidization to 315°, then treated with anhydrous hydrogen chloride for 9.6 min at 315°-337°, collecting 29.4 g chlorosilanes. After purging with nitrogen for 1.6 hr, the bed was cooled to room temperature and stored in the reactor under a positive nitrogen pressure for 3 days. It was then refluidized with nitrogen and heated to 256°. Ethanol (200 proof) and ammonia (anhydrous) were fed to the bed, replacing nitrogen, and fractions were collected as described in Table 7. The initial effect of the ammonia was to prevent initiation of the ethanol/silicon reaction. When ammonia was replaced by nitrogen at the end of fraction A, a vigorous ethanol reaction began at once, despite the nitrogen diluent. However, when ammonia was reintroduced in fraction C, the rate of silicon consumption fell off dramatically. During the fraction B, when the only reactant fed was ethanol, the mass became sticky, and good fluidization was unobtainable for the rest of the experiment. Ammonia was unable to prevent some fall-off mass activity, reflected by the lower silicon consumption rates in the last fractions. This example shows that ammonia does not have the beneficial effect on the ethanol/silicon reaction that is exhibited by dimethylamine, that ammonia retards the ethanol/silicon reaction rate, and that ammonia does not exhibit the beneficial effect of dimethylamine in prolonging mass life.

TABLE 6

Reaction of Ethanol and Monomethylamine with Silicon

A. Reaction Parameters

| Fraction | Duration (hr) | Temp (°C.) | Feed Rates [a] EtOH | $Me_2NH$ | $MeNH_2$ | $N_2$ | Crude Liquid Condensate (g) |
|---|---|---|---|---|---|---|---|
| A | 0.62 | 250-252 | 0 | 2940 | 0 | 290 | 0 |
| B | 0.67 | 253-254 | 0 | 2940 | 0 | 290 | 26.0 |
| C | 0.52 | 256-260 | 650 | 2940 | 0 | 290 | 63.1 |
| D | 0.33 | 259-262 | 1140 | 2940 | 0 | 290 | 56.0 |
| E | 0.30 | 258-262 | 1140 | 2940 | 36 | 290 | 36.6 |
| F 1 | 0.18 | 257-260 | 1140 | 2940 | 290 | 290 | } 47.1 |
| F 2 | 0.11 | 259-261 | 1140 | 2940 | 0 | 290 | |
| F 3 | 0.15 | 257-260 | 1110 | 1510 | 1370 | 290 | |
| G [b] | 0.46 | 257-260 | 1110 | 0 | 2780 | 290 | 39.8 |
| H 1 | 0.22 | 248-257 | 1110 | 2930 | 0 | 290 | } 33.9 |
| H 2 [c] | 0.07 | 248-252 | 0 | 2930 | 0 | 290 | |
| I | 0.43 | 252-253 | 0 | 2930 | 0 | 290 | 0.6 |

Notes:
[a] cm³/min at 250° C./787 Torr, calculated from room temperature measurements using ideal gas law.
[b] Loss of fluidization at bed bottom.
[c] Lower 1 cm of bed not fluidized B. Product Analysis

| Fraction | GLC Analysis [d] EtOH | TDS | TEOS | monomers [e] | heavies [f] | Mean Si Consumption Rate (% per hr) |
|---|---|---|---|---|---|---|
| B | — | 77.7 | — | 4.7 | 0.8 | 6.0 |
| C | 0 | 28.1 | 0.2 | 45.2 | 0.5 | 18.9 |
| D | 0 | 18.3 | 0.2 | 62.0 | 1.1 | 30.9 |
| E | 0 | 3.3 | 1.1 | 72.7 | 5.4 | 24.9 |
| F | 0 | 0.7 | 3.8 | 70.6 | 6.2 | 23.9 |
| G | 0.7 | 0 | 70.2 | 13.4 | 9.0 | 19.0 |
| H | 6.7 | 0 | 17.0 | 0.1 | 7.9 | 7.4 |

TABLE 6-continued

| | Reaction of Ethanol and Monomethylamine with Silicon | | | | | |
|---|---|---|---|---|---|---|
| I [g] | 40.9 | 0 | 6.0 | 1.6 | 6.6 | 0.1 |

Notes:
[d] Percent of total GLC peak area. Unaccounted for area is dimethylamine, monomethylamine, and unidentified peaks of retention time less than 2 min, except as noted.
[e] Unidentified peaks of retention times 2 min to 7.5 min (TEOS = 6.6 min).
[f] All peaks of retention time greater than 7.5 min.
[g] Also includes 16.7% bis(dimethylamino)methane (retention time 1.9 min)

TABLE 7

Effect of Ammonia

| Fraction | Temp. (°C.) [d] | Duration (hr) | Feed Rates [a] | | Crude liquid condensate (g) | Analysis [b] | | Si conversion (%/hr) | |
|---|---|---|---|---|---|---|---|---|---|
| | | | EtOH | NH$_3$ | | TEOS | heavies | total | to TEOS |
| A | 251–253 [c] | 0.41 | 83 | 77 [c] | 70.93 | .66 | .23 | 0.3 | 0.2 |
| B | 254–315 | 0.16 | 83 | 0 | 39.40 | 32.62 | 5.06 | 13.9 | 11.8 |
| C | 240–262 | 0.47 | 83 | 77 | 123.10 | 2.94 | 1.19 | 1.7 | 1.2 |
| D | 251–254 | 0.42 | 87 | 77 | 107.19 | 2.52 | 1.07 | 1.5 | 1.1 |
| E | 251–253 | 0.37 | 87 | 77 | 96.74 | 2.87 | 1.11 | 1.7 | 1.1 |
| F | 247–253 | 0.50 | 93 | 77 | 133.04 | 1.74 | .97 | 1.2 | 0.7 |
| G | 242–252 [e] | 0.48 | 90 | 77 | 133.24 | .86 | .56 | 0.6 | 0.4 |

[a] mmol/min
[b] gas chromatographic area percents. Remainder is non-Si-containing lites and unconsumed reactants.
[c] NH$_3$ was replaced by N$_2$ 0.04 hr before the end of fraction B. An exotherm began at once, reaching 270° by end-of-fraction.
[d] reflects temperature ca 5 cm above bed bottom. Temperature at bed bottom was up to 40° lower in the later fractions; when the mass was not fluidizing well at bed bottom.
[e] Ammonia flow was stopped ca 1 min before EtOH, and temperature began an immediate rise, reaching 258° before the EtOH flow was interrupted.

Various modifications and variations of this invention will be obvious to a worker skilled in the art. It is to be understood that such modifications and variations are to be included within the purview of this application and the spirit of the appended claims.

What is claimed is:

1. A process for the preparation of a tetraalkylorthosilicate with comprises (I) contacting at a temperature in the range of 200° C. through 350° C. for a period of time sufficient to form a silane mixture (A) an alkanol ROH wherein R is an alkyl group of from one to three carbon atoms and (B) dimethylamine with (C) copper-activated silicon, wherein the mole ration of dimethylamine (B) to alkanol (A) is in the range of from 0.2:1 to 10:1, and (II) subsequently adding to said silane mixture at least enough alkanol ROH to convert all of the silanes present to tetraalkylorthosilicates.

2. A process as in claim 1 wherein the mole ratio of dimethylamine to alkanol is from 0.8:1 to 5:1.

3. A process as in claim 2 wherein the mole ratio of dimethylamine to alkanol is from 1:1 to 3:1.

4. A process as in claim 3 in which the alkanol and dimethylamine are contacted with copper-activated silicon at a temperature in the range of 240° C. through 290° C. and in which excess alkanol is added to the resultant silane mixture at ambient temperature.

5. A process as in any one of the claims 1, 2, 3, or 4 in which the alkanol is ethanol.

* * * * *